United States Patent [19]

Fawzi

[11] 4,208,205
[45] Jun. 17, 1980

[54] HERBICIDAL BENZAMIDES
[75] Inventor: Maged M. Fawzi, Wilmington, Del.
[73] Assignee: E. I. Du Pont de Nemours and Company, Wilmington, Del.
[21] Appl. No.: 838,957
[22] Filed: Oct. 3, 1977
[51] Int. Cl.² ............................................. C07C 103/76
[52] U.S. Cl. .......................................... 71/118; 71/95; 71/98; 71/105; 260/558 S; 260/559 B; 260/559 R; 260/559 S; 260/562 P; 260/465 E; 260/326.5 J; 562/432; 562/473; 560/18; 560/64
[58] Field of Search ............ 260/558 S, 559 B, 559 R, 260/559 S, 465 E, 326.5 J, 562 P, 520 E; 71/118, 115, 95, 105, 98

[56] References Cited
U.S. PATENT DOCUMENTS

| 3,012,872 | 12/1961 | Richter | 71/118 X |
|---|---|---|---|
| 3,012,873 | 12/1961 | Richter | 71/118 X |
| 3,839,444 | 10/1974 | Theissen | 260/559 R |
| 4,063,929 | 12/1977 | Bayer et al. | 260/520 E X |

FOREIGN PATENT DOCUMENTS

| 240643 | 10/1964 | Austria | 71/115 |
|---|---|---|---|
| 2619489 | 11/1976 | Fed. Rep. of Germany | |
| 4827298 | 3/1968 | Japan | 260/559 R |
| 209445 | 1/1968 | U.S.S.R. | 71/118 X |

Primary Examiner—Arthur P. Demers

[57] ABSTRACT

Herbicidal compounds of the formula:

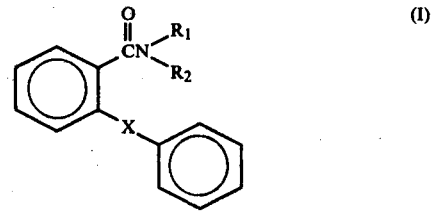

where
X is oxygen or sulfur;
$R_1$ is methyl or ethyl;
$R_2$ is alkyl of 1–4 carbon atoms, methoxy or cyanomethyl; and
$R_1$ and $R_2$ together can be $(CH_2)_4$; provided that when $R_2$ is alkyl of 3 or 4 carbon atoms, methoxy or cyanomethyl, $R_1$ cannot be ethyl.

28 Claims, No Drawings

HERBICIDAL BENZAMIDES

BACKGROUND OF THE INVENTION

U.S. Pat. No. 3,839,444 describes herbicidal compounds having the formula

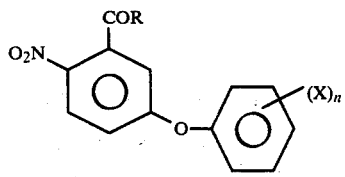

wherein
X is halogen,
n is 1 to 5, and
R is amido, alkylamido ($C_1$–$C_4$) or dialkylamido ($C_3$–$C_4$).

German Offenlegungsschrift No. 2,619,489 discloses compounds such as 3-Dimethylcarbamoyl diphenylether.

U.S.S.R. 209,445 describes the acylation of diphenylether with dimethylcarbamoyl chloride in the presence of aluminum chloride.

Although the abstract does not specify the position of the dimethylcarbamoyl group in the resulting product, it can be deduced that the resulting product is N,N-dimethyl-p-phenoxybenzamide.

Compounds such as those taught in U.S. Pat. No. 3,839,444 are active herbicides; the need still exists, however, for herbicides which are more active and more selective. The presence of undesired vegetation is very damaging to useful crops such as rice. In the current world situation, wherein food shortages are acute, it is most important not to lose a significant portion of a valuable crop such as rice. The presence of such undesired vegetation results in the loss of a significant portion of such crop. Thus, a need exists for a particularly effective herbicide which will destroy as much of this unwanted vegetation as is possible without causing significant damage to the desired crops, e.g., rice.

According to the instant invention, herbicidal compounds have been discovered which are highly active herbicides and yet cause minimal damage to certain desired crops.

DESCRIPTION OF THE INVENTION

This invention relates to novel compounds of Formula I, to their agricultural compositions and to their method of use as selective herbicides.

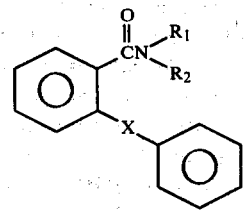

where
X is oxygen or sulfur;
$R_1$ is methyl or ethyl;
$R_2$ is alkyl of 1–4 carbon atoms, methoxy or cyanomethyl; and
$R_1$ and $R_2$ together can be $(CH_2)_4$; provided that when $R_2$ is alkyl of 3 or 4 carbon atoms, methoxy or cyanomethyl, $R_1$ cannot be ethyl.

Preferred for their high herbicidal activity or favorable cost or both are those compounds of Formula I where X is oxygen.

More preferred for their higher herbicidal activity or more favorable cost or both are those compounds of Formula I where $R_1$ is methyl; and $R_2$ is methyl or methoxy.

Specifically preferred for its outstanding herbicidal activity or favorable cost or both are: N,N-dimethyl-2-phenoxybenzamide and N-methoxy-N-methyl-2-phenoxybenzamide.

The invention also includes compositions containing the above compounds as active ingredients and methods for controlling barnyard grass by using the compounds and/or compositions.

DETAILED DESCRIPTION OF THE INVENTION

The starting materials for the compounds of this invention, namely, the 2-phenoxybenzoic acid and 2-(phenylthio)benzoic acid can be prepared from 2-halobenzoic acids and phenol as described in Ber., 38, 2112 (1905) and thiophenol as reported in CA. 63 2953h. The aforementioned preparative method can be readily understood by reference to the following reaction where X=O or S.

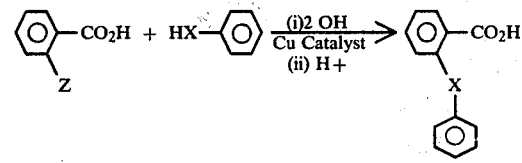

Z=Halogen

The substituted benzamides of this invention can be prepared from the appropriate acid by one of the following methods:

Method A

The acid is reacted with thionyl chloride in the presence of chloroform to give the 2-substituted benzoylchloride (see A. I. Vogel. A text-book of Practical Organic Chemistry, Longmans, Green and Co.—London, 1956, Page 792). The addition of the substituted benzoyl chloride to a solution of the amine in a suitable solvent such as methylene chloride, tetrahydrofuran, ether etc. or a mixture of solvents, such as water-ether, water-methylene chloride, in the presence of an acid acceptor, such as an excess of the amine, sodium hydroxide, potassium carbonate, triethylamine, pyridine, etc., gives the benzamide. This method can be represented by the following sequence of reactions where X, $R_1$ and $R_2$ have the same values as formula I.

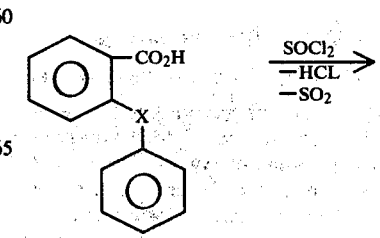

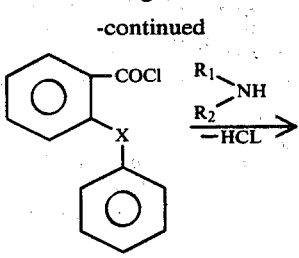

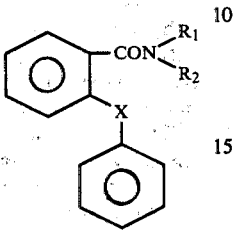

Method B

The acid is esterified with methanol or ethanol to give methyl or ethyl 2-substituted benzoate. Treatment of the ester with the appropriate amine gives the substituted benzamide.

This preparative method can be outlined in the following scheme where X, $R_1$, $R_2$ have the same values as in formula I

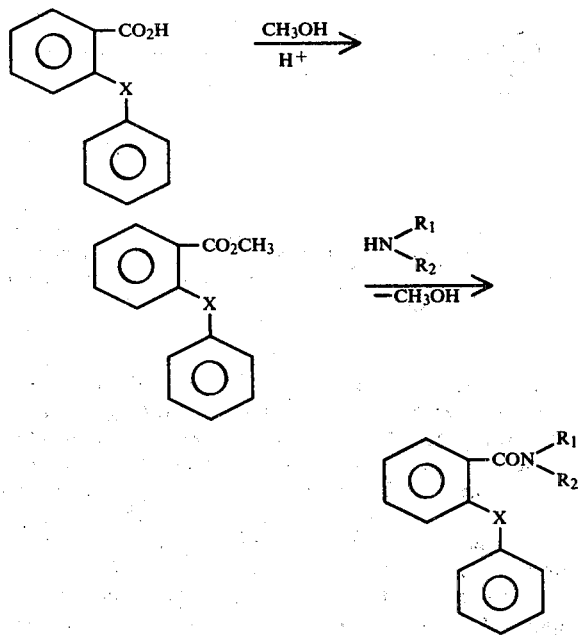

The following examples illustrate the preparation of compounds of this invention by method A. Unless otherwise stated parts are parts by weight and all temperatures are in °C.

EXAMPLE 1

Synthesis of N,N dimethyl-2-phenoxybenzamide

A solution of 7.7 parts of 2-phenoxybenzoyl chloride in 50 parts of methylene chloride was added slowly to a cold (0°) vigorously stirred mixture of 50 parts of methylene chloride and 40 parts of 25% aqueous dimethyl amine. After 8 hours the methylene chloride layer was separated. The organic layer was washed with water and dried over magnesium sulfate. Removal of the magnesium sulfate by filtration and the methylene chloride under vacuum gave 5.1 parts of N,N dimethyl-2-phenoxybenzamide as a viscous oil. NMR (CDCl$_3$) 2.9$\delta$(S,3H,N—CH$_3$), 3$\delta$(S,3H,N—CH$_3$), 7.2$\delta$(m,9H,Aromatic H).

EXAMPLE 2

Preparation of N-methoxy-N-methyl 2-(phenylthio)-benzamide

A solution of 3.7 parts of 2-(phenylthio)-benzoylchloride in 50 parts of tetrahydrofuran was added to a cold (~5°) stirred solution of 1 part N,O-dimethyl hydroxylamine and 1.6 parts triethylamine in 75 parts of tetrahydrofuran. The mixture was stirred for 8 hrs. and the temperature was allowed to rise to room temperature. Removal of the precipitated triethylamine hydrochloride by filtration and concentration of the filtrate under vacuum gave 3.3 parts of N-methoxy N-methyl 2-(phenylthio)-benzamide as a very viscous oil. NMR (CDCl$_3$) 3.3$\delta$(S,3H,N-CH$_3$), 3.5$\delta$(S,3H, O—CH$_3$), 7.3$\delta$(m,9H,Aromatic H).

EXAMPLE 3

Preparation of N-cyanomethyl, N-methyl-2-phenoxybenzamide 2.7 parts of methylaminoacetonitrile hydrochloride was added to a solution of 2 parts of sodium hydroxide in 25 parts of water at ~15°. When the addition was complete a solution of 5.8 parts of 2-phenoxybenzoyl chloride in 50 parts of methylene chloride was added dropwise. The mixture was stirred vigorously for 5 hrs. at ~20°. The methylene chloride layer was then separated, washed with water and dried over magnesium sulfate. Removal of the magnesium sulfate by filtration and concentration of the filtrate gave 4.6 parts of N-cyanomethyl-N-methyl-2-phenoxybenzamide as a viscous oil. NMR (CDCl$_3$) 3$\delta$(S,3H,CH$_3$), 4.1$\delta$,4.3$\delta$ (2S,2H,CH$_2$), 7.05$\delta$, (m,9H,Aromatic H).

EXAMPLE 4

Preparation of N-(2-phenoxybenzoyl)pyrrolidine 7.7 parts of 2-phenoxybenzoyl chloride was added dropwise to a solution of 2.5 parts of pyrrolidine in 20 parts of pyridine at 0°. When the addition was complete the mixture was stirred for 5 hours. The temperature was then allowed to rise to room temperature and the reaction mixture was poured into 100 parts of water. The aqueous solution was then extracted with chloroform, and washed with water. The chloroform layer was dried over magnesium sulfate, removal of the magnesium sulfate by filtration and concentration of the filtrate gave 6.4 parts of N-(2-phenoxybenzoyl)pyrrolidine, NMR (CDCl$_3$) 1.8$\delta$(m,4H,CH$_2$), 3.4$\delta$(m,4H-N-CH$_2$), 7.1$\delta$(m,9H,Aromatic H). The following compounds can be prepared from the 2-substituted benzoyl chloride and the appropriate secondary amine as described above.

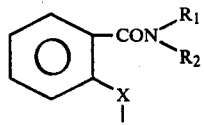

| X | R₁ | R₂ | NMR(CDCl₃) |
|---|---|---|---|
| O | $CH_3-$ | $CH_3O-$ | 3.2δ(S,3H,CH₃), |
|   |   |   | 3.5δ(S,3H,OCH₃) |
|   |   |   | 7.1δ(m,9H,Aromatic H) |
| O | $CH_3-$ | $C_2H_5-$ |   |
| O | $CH_3-$ | $n-C_3H_7-$ |   |
| O | $CH_3-$ | $iso-C_3H_7-$ |   |
| O | $CH_3-$ | $n-C_4H_9-$ | 0.9δ(t,3H,CH₃), |
|   |   |   | 1.5δ(m,4H,CH₂), |
|   |   |   | 2.9δ,3δ(2S,3H,CH₃), |
|   |   |   | 3.4δ(m,-2H,CH₂) |
|   |   |   | 7.1δ(m,9H,Aromatic H) |
| O | $CH_3-$ | $sec-C_4H_9-$ |   |
| O | $CH_3-$ | $iso-C_4H_9-$ |   |
| O | $CH_3-$ | $t-C_4H_9$ |   |
| O | $C_2H_5-$ | $C_2H_5-$ | 1.1δ,1.13δ(2t,6H,CH₃), |
|   |   |   | 3.42δ(2Q,4H,CH₂), |
|   |   |   | 7.1δ(m,9H,Aromatic H) |
| S | $CH_3-$ | $CH_3-$ | 2.8δ(S,3H,CH₃), |
|   |   |   | 3.1δ(S,3H,CH₃), |
|   |   |   | 7.25δ(m,9H,Aromatic H) |
| S | $CH_3-$ | $C_2H_5-$ |   |
| S | $CH_3-$ | $n-C_3H_7$ |   |
| S | $CH_3-$ | $iso-C_3H_7$ |   |
| S | $CH_3-$ | $n-C_4H_9-$ |   |
| S | $CH_3-$ | $sec-C_4H_9-$ |   |
| S | $CH_3-$ | $iso-C_4H_9-$ |   |
| S | $CH_3-$ | $t-C_4H_9-$ |   |
| S |   | $(CH_2)_4$ | 1.85δ(m,4H,CH₂), |
|   |   |   | 3.15δ,3.6δ(2m,4H,N—CH₂), |
|   |   |   | 7.3δ(m,9H,Aromatic H) |
| S | $C_2H_5-$ | $C_2H_5-$ | 1.0δ,1.1δ(2t,CH,CH₃), |
|   |   |   | 3.1δ,3.5δ(2q,4H,CH₂), |
|   |   |   | 7.3δ(m,9H,Aromatic H) |
| S | $CH_3-$ | $NCCH_2-$ |   |

Useful formulations of the compounds of Formula I can be prepared in conventional ways. They include granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. Most of the compounds of Formula I are liquids or heavy oils. Wettable powders and the other solid formulations made from these must be of lower strength than typical powders. The formulations, broadly, contain about 1% to 50% by weight of active ingredients(s) and at least one of a) about 0.1% to 20% surfactant(s) and b) about 5% to 99% solid or liquid diluent(s). More specifically, they will contain these ingredients in the following approximate proportions:

|   | Percent by Weight | | |
|---|---|---|---|
|   | Active Ingredient | Diluent(s) | Surfactant(s) |
| Wettable Powders | 15–40 | 50–84 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Granules and Pellets | 1–40 | 5–99 | 0–15 | of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, New Jersey. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N. J., as well as Sisely and Wood, "Encyclopedia of Surface Active Agents", Chemical Publ. Company, Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, New York, 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knüsli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 5

Wettable Powder

N,N-dimethyl-2-phenoxybenzamide: 25%
dioctyl sodium sulfosuccinate: 1.5%
sodium ligninsulfonate: 3%
low viscosity methyl cellulose: 1.5%
attapulgite: 69%

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 6

Granule

N,N-dimethyl-2-phenoxybenzamide: 10% attapulgite granules (low volatile matter, 0.71/0.30 mm; U.S.S. #25–50 sieves): 90%

The active ingredient is warmed to approximately 90° C. and sprayed upon dedusted and pre-warmed attapulgite granules in a double cone blender. The granules are then allowed to cool and are packaged.

EXAMPLE 7

Emulsifiable Concentrate

N,N-dimethyl-2-phenoxybenzamide: 30%
blend of oil soluble sulfonates and polyoxyethylene ethers: 4%
xylene: 66%

The ingredients are combined and stirred to speed solution. A fine screen filter is included in packaging operation to insure the absence of any extraneous undissolved material in the product.

Utility

The compounds of the present invention are useful for the selective control of undesired vegetation in cereal crops such as rice and wheat, and other crops. More particularly, the compounds of the present invention can be used for the control of weeds in paddy rice. These compounds are especially effective for preemergence weed control, and also can be used for postemergence weed control.

The compounds of this invention are useful for the control of weeds in transplanted crops such as rice, tobacco, tomatoes, cabbage, sweet potatoes, lettuce, celery, peppers, and eggplant. The treatment may be applied to the soil surface prior to transplanting and the crop transplanted through the treated soil or it may be soil incorporated prior to transplanting and the crop set in the treated soil. It may also be applied after the crop is transplanted although care should be taken to keep the chemical off the crop.

The precise amount of the compounds of the present invention to be used in any given situation will vary according to the particular end result desired, the use involved, the crop and weed species, and soil involved, the formulation used, the mode of application, prevailing weather conditions, foliage density and the like factors. Since so many variables play a role, it is not possible to state a rate of application suitable for all situations. Broadly speaking, the compounds of the invention are used at levels of about 0.05 to about 15 kilograms, preferably about 0.5 to about 10, per hectare. The lower rates in this range will generally be selected on lighter soils, soils low in organic matter content, or in situations where maximum persistence is not necessary.

Although the compounds of the present invention provide excellent weed control when applied as a sole herbicide treatment, they may also be advantageously applied in combination with other herbicides, including, but not restricted to, the following:

3-chloro-2-(4-chloro-2-fluorophenyl)-4,5,6,7-tetrahydro-2H-indazole
5-tert.-butyl-3-(2,4-dichloro-5-isopropoxyphenyl)-1,3,4-oxadiazol-2-one
S-(4-chlorobenzyl)-N,N-diethylthiolcarbamate
2,4-dichlorophenyl-3'-methoxy-4'-nitrophenyl ether
2-chloro-2',6'-diethyl-N-butoxymethyl-acetanilide
2-methylthio-4,6-bis(ethylamino)-S-triazine
S-ethylhexahydro-1H-azepine-1-carbothioate
3-isopropyl-1(H)-benzo-2,1,3-thiadiazin-4-one-2,2-dioxide
2,4-dichlorophenoxyacetic acid and closely related derivatives including salts.

The herbicidal activity of the compounds of this invention was discovered in greenhouse tests, conducted as described below:

Procedure Test 1

Seeds of crabgrass (Digitaria spp.), barnyardgrass (Echinochloa crusgalli), wild oats (Avena fatua), Cassia tora, morningglory (Ipomoea spp.), cocklebur (Xanthium spp.), sorghum, corn, soybean, rice, wheat and nutsedge tubers were planted in a growth medium and treated preemergence with the chemicals dissolved in a nonphytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including the cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

The ratings for compounds tested by this procedure are recorded in Table 1, and consist of a number and a letter. The number describes the extent of the response and ranges from zero to ten, with zero representing no response and ten representing 100% response. The letter described the type of response, with "B" representing burn (acute response), "C" chlorosis-necrosis (chronic response), "E" emergence inhibited, "G" growth retarded, "H" formative effect (malformation or hormone type), and "X", axillary stimulation. However, the combined rating "6Y" is an exception to the extent and type explanation above, and simply represents abscised buds or flowers.

TABLE I

| | | POST EMERGENCE | | | | | | | | | | | | | |
|---|---|---|---|---|---|---|---|---|---|---|---|---|---|---|---|
| Compound | Kg. Per Ha. | Bush Beans | Cotton | Sorghum | Corn | Soybean | Wheat | Wild Oats | Rice | Barnyardgrass | Crabgrass | Morning Glory | Cocklebur | Cassia | Nutsedge |
| 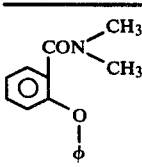 | 2 | 1B | 0 | 1B 6G | 2C 6G | 1B 3H | 6C | 7C | 1B 3G | 3C 6G | 1C 6G | 1B | 1B | 3B | 6G |

TABLE I-continued
| Structure | | | | | | | | | | | | | | |
|---|---|---|---|---|---|---|---|---|---|---|---|---|---|---|
| 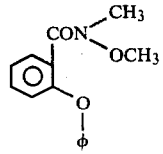 CON(CH₃)(OCH₃), o-OPh | 2 | 4B | 1B | 2B | 1B | 2B | 3B | 1B | 1B | 3B | 1B | 5C | 1B | 1B | 7G |
| 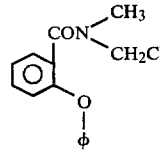 CON(CH₃)(CH₂CN), o-OPh | 2 | 2C | 1C | 1B | 1B | 0 | 4B | 2B | 0 | 2B | 1B 5G | 1B | 0 | 1B | 5G |
| 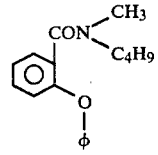 CON(CH₃)(C₄H₉), o-OPh | 2 | 0 | 1B | 1B | 0 | 1B | 1B | 1B | 0 | 1B | 0 | 1B | 0 | 1B | 0 |
| 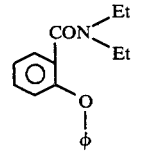 CON(Et)(Et), o-OPh | 2 | 1B 6Y | 2B | 1B | 1B | 1B 3H | 4C | 1B | 1B | 1B | 1B | 1B | 1B | 1B | 3C 7G |
| 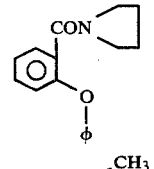 CON-pyrrolidine, o-OPh | 2 | 1C | 2G | 1B | 0 | 1B 5H | 0 | 0 | 1B | 1B | 1B | 1B | 2B | 1B | 0 |
| 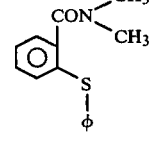 CON(CH₃)(CH₃), o-SPh | 2 | 1B | 1B | 1B | 2B | 2B 8X | 3B | 1B | 1B | 3B | 1B 5G | 1B | 1B | 1B | 7G |
| 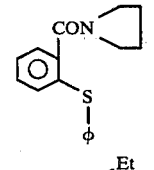 CON-pyrrolidine, o-SPh | 2 | 1B 6Y | 1B | 1B | 1B | 2B | 3B | 1B | 1B | 1B | 1B | 1B | 0 | 1B | 0 |
| 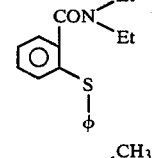 CON(Et)(Et), o-SPh | 2 | 2C | 0 | 1B | 1B | 4B | 3B | 1B | 1B | 2B | 1B | 1B | 0 | 3B | 0 |
| 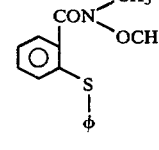 CON(CH₃)(OCH₃), o-SPh | 2 | 0 | 1B | 1B | 1B | 2B | 2B | 1B | 1B | 2B | 1B | 0 | 0 | 1B | 0 |
| 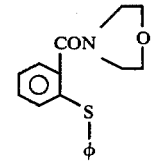 CON-morpholine, o-SPh | 2 | 2C | 1B | 1B | 1B | 1B | 2B | 1B | 1B | 1B | 1B | 0 | 10C | 1B | 0 |

TABLE I-continued
| Compound | Kg. Per Ha. | PRE-EMERGENCE |||||||||||
|---|---|---|---|---|---|---|---|---|---|---|---|---|
| | | Sorghum | Corn | Soybean | Wheat | Wild Oats | Rice | Barnyardgrass | Crabgrass | Morning Glory | Cocklebur | Cassia | Nutsedge |
| 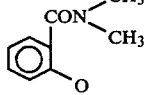 | 2 | 9H | 1C 7G | 2H 6G | 9H | 9H | 10E | 10E | 10E | 5H | 8C | 8G | 10E |
| 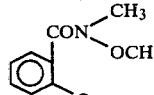 | 2 | 8C | 9C | 3C | 9H | 8H | 5C | 10C | 8C | 10C | 10C | 1C | 8G |
| 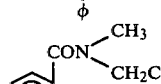 | 2 | 1C 6G | 2C 8G | 5G | 9G | 2C 6H | 7H | 9C | 7G | 1C | 3C | 0 | 9G |
| 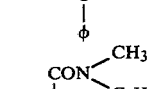 | 2 | 3G | 2C 6G | 0 | 5G | 5H | 0 | 10C | 0 | 0 | 0 | 0 | 5G |
| 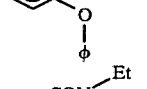 | 2 | 4C | 7C | 1C 6G | 3C 8G | 3C 6G | 7C | 10C | 5G | 3C | 0 | 3C | 6G |
| 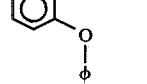 | 2 | 3G | 2G | 1C 8G | 0 | 0 | 1C | 9C | 1C 8G | 0 | 0 | 2G | 8G |
| 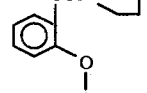 | 2 | 7G | 9H | 8G | 9H | 7G | 10E | 10E | 8G | 0 | 2G | 10C | 10E |
| 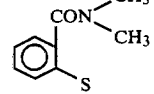 | 2 | 0 | 0 | 0 | 0 | 0 | 0 | 9C | 0 | 0 | 0 | 2G | 0 |
| 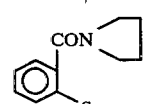 | 2 | 0 | 1C 5G | 2G | 4G | 4G | 2G | 9C | 0 | 0 | 0 | 0 | 0 |
| 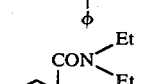 | 2 | 2C | 6G | 2G | 5G | 5G | 5C | 2C 8G | 5G | 5C | 0 | 5G | 9G |
| 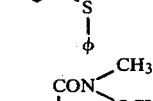 | 2 | 2G | 2G | 4G | 5G | 3G | 7G | 5C 9G | 0 | 5G | 0 | 2G | 0 | japonica rice plants which were transplanted into the paddy soil when in the three to four leaf stage. The water level was maintained a few centimeters above the soil surface. The test sample was applied directly into the paddy water, and plant response ratings were taken about three weeks later.

TABLE 3

| COMPOUND | Rate kg ai/ha | Japonica Rice | Barnyard-grass |
|---|---|---|---|
| 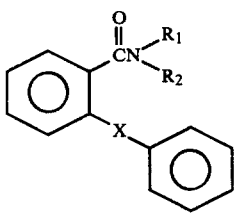 | 1/32 | 0 | 7C |
| | 1/16 | 0 | 8C |
| | ⅛ | 0 | 9C |
| | ¼ | 0 | 10C |

What is claimed is:
1. A compound of the formula where
X is oxygen or sulfur;
R₁ is methyl or ethyl;
R₂ is alkyl of 1–4 carbon atoms, methoxy or cyanomethyl; and
R₁ and R₂ together can be (CH₂)₄; provided that when R₂ is alkyl of 3 or 4 carbon atoms, methoxy or cyanomethyl, R₁ cannot be ethyl.

2. A compound of claim 1 wherein X is oxygen.
3. A compound of claim 2 wherein R₁ is methyl.
4. A compound of claim 2 wherein R₂ is methyl or methoxy.
5. A compound of claim 2 wherein R₁ is methyl and R₂ is methyl or methoxy.
6. The compound of claim 2 N,N-dimethyl-2-phenoxybenzamide.
7. The compound of claim 2, N-methoxy-N-methyl-2-phenoxybenzamide.
8. A composition for the control of undesirable vegetation consisting essentially of the compound of claim 1 and at least one of (a) a surface-active agent and (b) a solid or liquid diluent.
9. A composition for the control of undesirable vegetation consisting essentially of a compound of claim 2 and at least one of (a) a surface-active agent and (b) a solid or liquid diluent.
10. A composition for the control of undesirable vegetation consisting essentially of a compound of claim 3 and at least one of (a) a surface-active agent and (b) a solid or liquid diluent.
11. A composition for the control of undesirable vegetation consisting essentially of a compound of claim 4 and at least one of (a) a surface-active agent and (b) a solid or liquid diluent.
12. A composition for the control of undesirable vegetation consisting essentially of a compound of claim 5 and at least one of (a) a surface-active agent and (b) a solid or liquid diluent.
13. A composition for the control of undesirable vegetation consisting essentially of the compound of claim 6 and at least one of (a) a surface-active agent and (b) a solid or liquid diluent.
14. A composition for the control of undesirable vegetation consisting essentially of a compound of claim 7 and at least one of (a) a surface-active agent and (b) a solid or liquid diluent.
15. A method for the control of undesirable vegetation comprising applying to the locus of such undesirable vegetation a herbicidally effective amount of a compound of claim 1.
16. A composition for the control of undesirable vegetation comprising applying to the locus of such undesirable vegetation a herbicidally effective amount of a compound of claim 2.
17. A method for the control of undesirable vegetation comprising applying to the locus of such undesirable vegetation a herbicidally effective amount of a compound of claim 3.
18. A method for the control of undesirable vegetation comprising applying to the locus of such undesirable vegetation a herbicidally effective amount of a compound of claim 4.
19. A method for the control of undesirable vegetation comprising applying to the locus of such undesirable vegetation a herbicidally effective amount of a compound of claim 5.
20. A method for the control of undesirable vegetation comprising applying to the locus of such undesirable vegetation a herbicidally effective amount of the compound of claim 6.
21. A composition for the control of undesirable vegetation comprising applying to the locus of such undesirable vegetation a herbicidally effective amount of the compound of claim 7.
22. A method for the control of barnyard grass in rice comprising applying to the locus of such barnyard grass a herbicidally effective amount of a compound of claim 1.
23. A method for the control of barnyard grass in rice comprising applying to the locus of such barnyard grass a herbicidally effective amount of a compound of claim 2.
24. A method for the control of barnyard grass in rice comprising applying to the locus of barnyard grass a herbicidally effective amount of a compound of claim 3.
25. A method for the control of barnyard grass in rice comprising applying to the locus of such barnyard grass a herbicidally effective amount of a compound of claim 4.
26. A method for the control of barnyard grass in rice comprising applying to the locus of such barnyard grass a herbicidally effective amount of a compound of claim 5.
27. A method for the control of barnyard grass in rice comprising applying to the locus of such barnyard grass a herbicidally effective amount of the compound of claim 6.
28. A method for the control of barnyard grass in rice comprising applying to the locus of such barnyard grass a herbicidally effective amount of the compound of claim 7.

* * * * *